(12) United States Patent  
Pichon et al.

(10) Patent No.: US 9,030,554 B2
(45) Date of Patent: May 12, 2015

(54) DEVICE FOR ANALYSING THE SURFACE OF A SUBSTRATE

(75) Inventors: Michel Pichon, Gouvieux (FR); Franc Davenne, Thourotte (FR)

(73) Assignee: Saint-Gobain Glass France, Courbevoie (FR)

( * ) Notice: Subject to any disclaimer, the term of this patent is extended or adjusted under 35 U.S.C. 154(b) by 436 days.

(21) Appl. No.: 13/122,091

(22) PCT Filed: Sep. 29, 2009

(86) PCT No.: PCT/FR2009/051838
§ 371 (c)(1),
(2), (4) Date: Mar. 31, 2011

(87) PCT Pub. No.: WO2010/037958
PCT Pub. Date: Apr. 8, 2010

(65) Prior Publication Data
US 2011/0187855 A1    Aug. 4, 2011

(30) Foreign Application Priority Data
Oct. 1, 2008   (FR) ...................................... 08 56628

(51) Int. Cl.
*H04N 7/18*  (2006.01)
*G01B 11/25*  (2006.01)
*G01N 21/896*  (2006.01)
*G01N 21/958*  (2006.01)

(52) U.S. Cl.
CPC .......... *G01B 11/2513* (2013.01); *G01N 21/896* (2013.01); *G01N 21/958* (2013.01); *G01N 2021/9586* (2013.01)

(58) Field of Classification Search
None
See application file for complete search history.

(56) References Cited

U.S. PATENT DOCUMENTS

| 5,003,187 A | 3/1991 | Zumbrunn et al. |
| 5,471,297 A | 11/1995 | Tani |

(Continued)

FOREIGN PATENT DOCUMENTS

| EP | 0 726 457 | 8/1996 |
| EP | 1 065 498 | 1/2001 |
| EP | 1 577 641 | 9/2005 |

OTHER PUBLICATIONS

Salvi J. et al. "Pattern codification strategies in structured light systems." Pattern Recognition, vol. 37, No. 4. pp. 827-849 (Apr. 2004) XP 4491495.

(Continued)

*Primary Examiner* — Sath V Perungavoor
*Assistant Examiner* — Kate Luo
(74) *Attorney, Agent, or Firm* — Oblon, McClelland, Maier & Neustadt, L.L.P.

(57) ABSTRACT

An analysis device for analysing a transparent or specular surface of a substrate, the device including a raster located opposite the surface of the substrate to be measured, a video camera for capturing at least one image of the raster deformed by the measured substrate, a raster lighting system, and an image-processing and digital analysis mechanism connected to the video camera. The video camera is a matrix array camera, the raster is provided on a substrate having an oblong shape and is bidirectional including a first pattern extending along a first direction and along a smallest extension of the substrate, the first pattern being transversely periodical to the smallest extension, and a second pattern extending in a second direction perpendicular to the first pattern and along a largest extension of the substrate.

11 Claims, 1 Drawing Sheet

(56) References Cited

U.S. PATENT DOCUMENTS

| | | | |
|---|---|---|---|
| 5,471,307 A | 11/1995 | Koliopoulos et al. | |
| 5,691,811 A | 11/1997 | Kihira | |
| 6,100,990 A | 8/2000 | Ladewski | |
| 6,208,412 B1 | 3/2001 | Ladewski | |
| 6,392,754 B1 | 5/2002 | Pingel et al. | |
| 6,541,169 B1 * | 4/2003 | Okino et al. | 430/30 |
| 6,611,343 B1 | 8/2003 | Frankowski | |
| 7,495,760 B2 * | 2/2009 | Miyake et al. | 356/239.1 |
| 2005/0200857 A1 | 9/2005 | Christ et al. | |
| 2008/0156780 A1 * | 7/2008 | Voronov et al. | 219/121.69 |
| 2008/0228419 A1 * | 9/2008 | Renken | 702/81 |

OTHER PUBLICATIONS

International Search Report issued Feb. 17, 2010 in PCT/FR09/51838 filed Sep. 29, 2009.

U.S. Appl. No. 13/637,318, filed Sep. 25, 2012, Pichon, et al.

* cited by examiner

DEVICE FOR ANALYSING THE SURFACE OF A SUBSTRATE

The invention relates to a device for analysing the specular or transparent surface of a substrate, making it possible in particular to detect optical defects either on the surface of this substrate or within the volume thereof.

In general, it is sought in industry to achieve ever greater control of the quality of manufactured products. In particular, there is at present a need for permanently evaluating the level of optical quality of glazing panels.

In particular, it may be desirable to select the flat glass leaving production lines in order to use it for a particular application, such as for example a mirror intended for scientific applications, a laminated glazing panel intended for the building industry, an automotive glazing panel, such as a windscreen intended in particular to be highly inclined, or a flat thin glass intended for a display screen.

In general, modern motor vehicle windscreens are particularly monitored as regards their optical quality. This criterion specifically addresses the problem of motor vehicle driving safety. Therefore the shape of windscreens, their angle of inclination and the manufacturing materials—which are very thin glasses or even transparent polymers—require very careful inspection of the optical quality, which often has to be 100% inspection.

Laminated automotive glazing panels require two glass sheets of small thickness compared with a toughened or tempered monolithic glazing panel. The production of such thin glass sheets is tricky and may lead to optical defects on the surface or within the volume. These defects may become very problematic after assembly for forming a laminated glazing panel since they cause optical distortion effects that are accentuated owing to a second glass sheet being joined thereto. The presence of such optical defects often results in the glazing panels being scrapped because they are unacceptable. Because the glazing panels have already been laminated, it is difficult to recycle them and their production cost becomes too high.

It is therefore also desirable to detect such defects as rapidly as possible on the manufacturing line and in particular before assembling a laminated glazing panel.

The optical defects are often two-dimensional defects, these may be substrate flatness defects for example or defects within the volume of the substrate due for example to the composition of the glass, these defects causing light passing through the substrate to deviate.

Also found are defects along a single direction, such as float waves that correspond to the signature of the forming process on the float line, these defects being greater or larger/smaller in size depending on the quality of the forming process.

The techniques normally used for detecting and evaluating defects consist in observing the laminated glazing panel in transmission or in reflection using standardized techniques, such as by visual observation after assembly of the laminated glazing panel and away from the manufacturing line. As explained above, such inspection is slow and in particular increases the production cost.

Moreover, specular and transparent surface inspection techniques are commercially available which make it possible to detect surface defects by measurements in reflection or in transmission of the glazing panel reflecting the distorted pattern of a reference pattern.

U.S. Pat. No. 6,509,967 describes a method for detecting optical defects based on analysing the distortions of a two-dimensional reference pattern observed in transmission. In the case of defects, the image of the reference pattern is distorted, and the distortion of numerous points of the image is measured so as to deduce therefrom, by calibration, the optical power along two directions, the values of which are representative of the presence or absence and the magnitude of said defects. This document insists on the need for studied coupling of the reference pattern relative to the camera responsible for the image acquisition in transmission. Each line of the reference pattern must correspond to an integral number of lines of pixels of the camera.

However, the method of this United States patent requires the characteristics of the reference pattern (its dimensions, its shapes and its position) to be known or adapted so as to ensure that the pattern of the reference pattern is suitably aligned with the pixels of the camera. Such an alignment is restricting and rarely possible in an industrial environment (poor regularity of the reference pattern, expansion of the reference pattern with the variations in temperature over the day, floor vibrations, etc.).

U.S. Pat. No. 6,208,412 provides another measurement method in which a one-dimensional reference pattern is observed in transmission. The measurement device of the above document uses a projector to generate a reference pattern which forms, on a large screen, always substantially greater than the size of the glazing panel to be measured (typically 2×3 m), a one-dimensional periodic pattern which is fixed or can vary in time, and also a camera that displays the reference pattern through the glazing panel to be analysed.

The device described in the latter document, although it may be satisfactory in the laboratory or on edge of a production line for quality control by taking samples, cannot however be used for on-line inspection which has to be exhaustive and carried out without the glazing panels being able to be momentarily stopped.

The incorporation of a projector and a large screen on an industrial line is also rarely possible or desirable, for lack of space. Moreover, the image produced by a projector is in general not very bright. It is therefore essential to shield the screen from spurious ambient light by extensively covering it and even painting the floor black.

Furthermore, to measure defects in two directions in space, since the reference pattern is one-dimensional, the measurement device requires acquisition of a first image with the reference pattern oriented in a given direction and then a second image with the reference pattern oriented in a perpendicular direction, necessitating the glazing panel stopping during the acquisition, something which is not conceivable on an industrial line, such as for motor vehicles, the glazing panel conveying system of which precludes a temporary stop.

Finally, the measurement method described is a well-known phase-shifting method which consists, with the glazing panel stopped, in successively projecting several, typically four, reference patterns that are offset in space and in acquiring an image for each reference pattern position, these operations being repeated a second time for the other measurement direction. This series of acquisitions is therefore very time-consuming and further extends the time during which the glazing panel is stopped.

Consequently, the device described in this patent U.S. Pat. No. 6,208,412 and its measurement procedure entail measurement processing times that are too long considering the very short times that are imposed on industrial lines for taking the decision to retain or to reject a glazing panel.

The Applicant was thus given the mission of designing a device for analysing the optical quality of a specular or transparent substrate that does not have the drawbacks of the abovementioned techniques and makes it possible to detect and quantify defects of this substrate in transmission or in reflection, in an easy, precise and repetitive manner while still meeting all the constraints of implementation on an industrial line for exhaustive inspection of the glazing panels and in particular by reducing the cost of glazing panel conformity inspection on a production line. This innovative device must furthermore make it possible to use measurement methods that result in the analysis time being optimized.

According to the invention, the device for analysing a transparent or specular surface of a substrate comprises a reference pattern facing the surface of the substrate to be measured and placed on a support with two dimensions of short and long extents, a camera for capturing at least one image of the reference pattern distorted by the measured substrate, a reference pattern illumination system and image processing/digital analysis means which are connected to the camera and is characterized in that the support has an oblong shape and the reference pattern is bidirectional, consisting of a first pattern that lies along a first direction and along the shorter extent of the support, this first pattern being periodic transverse to the short extent, and of a second pattern that lies along a second direction, perpendicular to the first pattern and along the longer extent of the support, and in that the camera is a matrix camera.

It will be recalled that a matrix camera is composed of a sensor which forms a matrix of pixels.

The oblong shape of the support of the reference pattern accompanied by the use of a matrix camera makes it possible highly advantageously to reduce the area occupied by the reference pattern and thus limit the space necessary for the device on a production line. Furthermore, the use of a reference pattern having two patterns extending in two different directions permits direct measurement of the defects that may be oriented in the substrate along two directions in space.

The magnitude of the patterns of the reference pattern and the position of the reference pattern, the glass and the camera are of course to be adapted to each type of measurement, which may just as well be the inspection of glazing panels measuring 2 m by 2 m (or more) or solar mirrors as the inspection of glass samples not exceeding 5 cm by 5 cm in size.

According to one feature, the first pattern and the second pattern are distinct, in the immediate vicinity of and not intersecting each other.

According to another feature, the first pattern is composed of an alternating succession of light and dark lines.

According to another feature, the second pattern is formed from a succession of light and dark oblong lines, the longer dimension of which lies along the long extent of the support.

According to another feature, the second pattern is formed from a single oblong line, the longer dimension of which lies along the long extent of the support, this line having a contrasted colour relative to the background of the reference pattern.

The second pattern, which may be of the order of one millimetre in the case of a single line or a few millimetres in the case of a succession of a few lines, implies consequently a minimization of the reference pattern.

The width of the elements (for example lines) forming each pattern is in fact adapted according to the measurement conditions and the magnitude of the defects. Preferably, the first pattern and/or the second pattern comprise/comprises at least one line which has, along its short extent, a width of the order of 1 mm to 1 cm. For measurements in reflection on solar mirrors, the lines of the pattern are for example of the order of 1 cm in width, whereas for measurements in transmission on glazing panels, the lines are of the order of one millimetre in width.

Furthermore, if the support for the reference pattern consists of a panel back-lit by the illumination system, the support panel for the reference pattern may then not exceed 15 cm in width, therefore considerably reducing the dimensions for installing the device of the invention compared with the existing ones.

As back-lit panel, the panel is, on its face turned towards the substrate to be measured, translucent and diffusing. For example, it is a white plastic sheet.

Advantageously, and in particular in the case of backlighting, the illumination system is formed from numerous light-emitting diodes.

To take a measurement in transmission, the substrate is positioned between the reference pattern and the camera, whereas the substrate is placed facing the reference pattern and the camera for a measurement in reflection, the camera being in the same plane as the reference pattern.

The small dimensions of the reference pattern compared with the substrate that is to be measured in its entirety mean that the reference pattern or the substrate can be moved during the measurement.

Thus, compared with the prior art for measurements on large products such as glazing panels, the reference pattern does not need to be as extensive in both directions as, or even larger than, the glazing panels. According to the invention, it is sufficient to provide an oblong reference pattern, the long extent of which corresponds at most to the height of the object to be measured and the short extent of which is extremely small compared with the other dimension of the object, combined with a matrix camera.

To meet the need for defects to be analysed simultaneously in two (vertical and horizontal) directions, the device uses a back-lit double-pattern reference pattern, one consisting of a single vertical line or of very few vertical lines, the other consisting of a series of very short (typically 5 cm) uniformly spaced horizontal lines, and a matrix camera, only the columns of pixels of which that are associated with each of the two reference patterns will be sampled after acquisition of the image.

This technique applies both to measurements in transmission and to measurements in reflection.

The invention also relates to a method of analysing a transparent or specular surface of a substrate using the device of the invention, the substrate or the reference pattern moving one relative to the other along a single displacement direction, characterized in that it consists in:

capturing, using the matrix camera, numerous images of the illuminated reference pattern in transmission or in reflection;

spatially extracting in a periodic manner, on the one hand, a column of pixels associated with the periodic first pattern and, on the other hand, several columns of pixels associated with the second pattern;

stacking, in memory, the columns of pixels for each of the patterns so as to reconstruct the image of the entire substrate;

analysing the reconstructed image by digital processing so as to deduce therefrom the position of defects and to quantify them.

The principle of the proposed method consists no longer in acquiring, through a substrate at rest, a single image of a multi-line reference pattern projected onto a large screen but in acquiring a series of several images of a very narrow reference pattern seen through or in reflection from a substrate in translation and in grouping these partial images so as to reconstruct the complete image of the reference pattern seen through or reflected by the substrate.

The digital processing of the image is then carried out in a known manner. This involves for example extracting local phases of the image and deducing therefrom phase variations that make it possible not only to deduce the position of defects but also to quantify them thanks to calibration or distortion coefficients with which a magnitude of the distortion or an optical power representative of the defects may be provided.

It should be noted that the digital phase extraction processing may be carried out in various ways using the Fourier transform method or the contour search method or else, in a novel manner, the wavelet transform method.

It appears that the method according to the invention gives satisfactory results on industrial lines, without modifying the latter, for lower cost, and permits much more rapid inspection than in the prior art.

The device of the invention and the method of implementation may be applied to transparent substrates, such as monolithic or laminated, flat or curved, glazing panels of any size for various (architectural, automotive, aeronautical, railway) uses or such as mirrors or display screens. In particular, the device and the method may be applied in transmission to motor vehicle windscreens, side windows and heated rear windows, to flat glazing panels intended for architectural applications or to special glazing panels intended for electronic applications (plasma or LCD displays, etc.) and to any other transparent substrate. The device may be used in reflection to qualify the optical quality of flat glass, for example in real time as the glass leaves the float bath, or of curved glass as it leaves for example the tempering furnace, of solar mirrors, etc.

The present invention will now be described with the aid of purely illustrative examples that do not in any way limit the scope of the invention and on the basis of the appended illustrations in which.

The figures have not been drawn to scale in order to make it easier to examine them.

Figure 1:
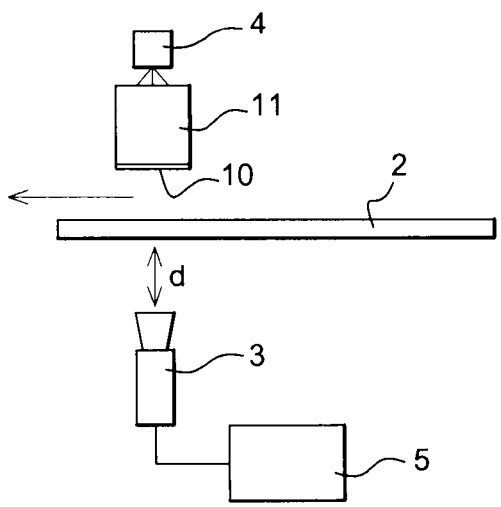
FIG. 1 shows a schematic sectional view of an analysis device according to the invention for a measurement in transmission.
Figure 2:
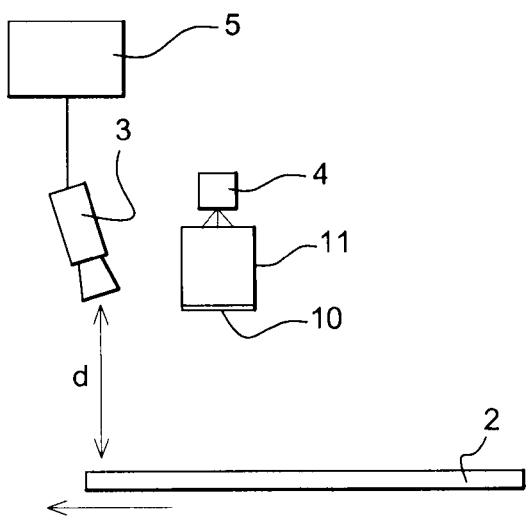
FIG. 2 shows a schematic sectional view of an analysis device according to the invention for a measurement in reflection.

The device 1 illustrated in FIGS. 1 and 2 permits analysing, in transmission and in reflection respectively, the defects of a transparent substrate 2, such as a glazing panel. The device comprises a reference pattern 10, image capture means 3, such as a matrix camera, a reference pattern illumination system 4 and suitable processing/computation means 5.

The reference pattern 10 is formed on one face of a support panel 11 facing the substrate to be measured. It will be described more fully later.

In transmission (FIG. 1), the transparent substrate 2 is placed between the reference pattern 10 and the camera 3, the objective lens of the camera being directed towards the substrate.

In reflection (FIG. 2), the substrate 2 having a specular surface is placed in front of the reference pattern 10 and the camera 3, the objective lens of the camera being in the same plane as that of the reference pattern and being pointed towards the surface of the substrate. If an angle of observation has to be imposed so as to be placed under the conditions in which the product to be measured will be finally used, for example an inclined glazing panel used as a vehicle windscreen, the angle of the camera relative to the plane of displacement of the substrate corresponds to the imposed angle of the reference pattern relative to this plane of displacement of the glazing panel.

The illumination system 4 may be a back-lighting system when the support panel 11 is translucent, such as a white plastic sheet. Preferably, the illumination system 4 then consists of numerous light-emitting diodes that are positioned to the rear of the translucent support panel.

As a variant, when the support panel 11 is opaque, the illumination system 4 is formed from a light placed to the front of the reference pattern, for example a spot (not illustrated) oriented so as to illuminate the front face of the support panel bearing the reference pattern.

The camera 3 is a matrix camera: it generates image frames which, by digital processing, are concatenated to form an overall image of the substrate. Since the reference pattern is small compared with the substrate, as will be seen later, the substrate 2 or the reference pattern 10 is able to be displaced in translation one relative to the other so as to ensure the requisite number of image acquisitions over the entire substrate. The frequency with which the camera is triggered for each image acquisition is slaved to the speed of displacement.

The camera is positioned at a suitable distance d so as to display the entire extent of the substrate, which is transverse to the direction of displacement of the substrate or the reference pattern. Thus, if the displacement is in a horizontal plane, the camera is placed so as to photograph the entire vertical extent of the substrate.

The camera 3 could make an angle to the vertical adapted to the conditions under which the substrate will be finally used, for example if the substrate is then used as a vehicle windscreen and therefore inclined to the vertical plane of viewing of the driver/observer.

Figure 3:
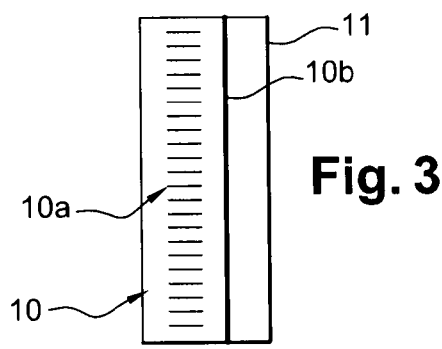
FIG. 3 illustrates an example of a reference pattern according to the invention.

The reference pattern 10, as illustrated in FIG. 3, is placed on a support 11 of oblong shape. It is bidirectional and consists of a first pattern 10a and a second pattern 10b placed in the immediate vicinity of each other but with no overlap.

The reference pattern according to the invention is small compared with the substrate to be measured. For example, for measuring a glazing panel with dimensions of 1.5 m by 1.5 m, the reference pattern extends over 15 cm by 1.8 m for a zero angle of inclination of the glazing panel. For measurement at a 45° angle of inclination of the glazing panel (in the driving position for a windscreen), the height will be 1.3 m.

The first pattern 10a of the reference pattern lies along a first direction and along the shorter extent of the support, being periodic transverse to the short extent, i.e. periodic along the long extent of the support. The second pattern 10b lies along a second direction, perpendicular to the first pattern and along the longer extent of the reference pattern.

The fact that the reference pattern has two separate patterns in the immediate vicinity of each other, but not overlapping, and perpendicular to each other, makes it possible for the position of defects to be precisely diagnosed and quantified in minute detail. This separation of the patterns makes it possible in particular to have a pattern of very narrow width, such as a dark vertical line 2 mm in width.

The first pattern 10a is composed of an alternating succession of light and dark lines.

The second pattern 10b is preferably formed from a limited number of contrasted lines, which alternate but together remain of small width. Thus, the second pattern is for example formed from around ten dark lines alternating with around ten light lines. The dark lines and the light lines have for example a width of between 1 mm and 2 mm over the entire height of the reference pattern.

As a variant, the second pattern may comprise a single oblong line, for example 1 mm in width, over the height of the reference pattern, this line being contrasted relative to the background of the reference pattern.

The processing/computation means 5 are connected to the camera so as to carry out the mathematical processing and analyses that follow the successive image acquisitions.

Figure 4:
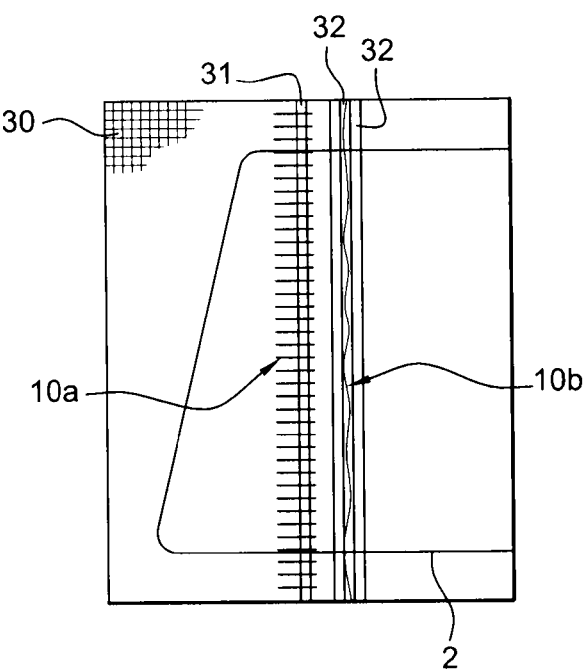
FIG. 4 illustrates an image of the reference pattern recorded by the camera.

FIG. 4 illustrates an image recorded by the camera, the image of the reference pattern being distorted by the presence of defects in two directions. The implementation of the device, the substrate or the reference pattern moving one relative to the other along a single displacement direction, consists in:
- capturing, using the matrix camera 3 having numerous pixels 30, numerous images of the illuminated reference pattern in transmission or in reflection;
- spatially extracting in a periodic manner, on the one hand, a column 31 of pixels associated with the periodic first pattern and, on the other hand, several columns 32 of pixels associated with the second pattern;
- stacking, in memory, the columns of pixels for each of the patterns so as to reconstruct the image of the entire substrate;
- analysing the reconstructed image by digital processing so as to deduce therefrom the position of defects and to determine their magnitude.

Acquisition of a series of n images of the line forming for example the vertical second pattern, during horizontal displacement of the substrate in front of the reference pattern, makes it possible to reconstruct, by simple concatenation of images, a single image equivalent to that which would be obtained by observing just once the image of a reference pattern consisting of n lines placed behind the substrate. The Applicant has demonstrated that this type of reference pattern is particularly advantageous because of its limited size.

A reference pattern is a spatially periodic signal. The mathematical analysis consists in characterizing in a known manner this signal by its local phase modulo $2\pi$, at a pixel of the camera, and a one-dimensional map of the phases (corresponding to all the pixels) of each of the images seen in transmission or in reflection, called a phase map, is thus defined.

This extraction of the phase map modulo $2\pi$ can be obtained using various methods.

One well-known method is the Fourier transform method, widely described in the literature. It can thus be divided into:
- acquisition of an image of the reference pattern distorted by the specimen;
- calculation of the Fourier transform of the image, pixel column by pixel column (one-dimensional transform);
- automatic search for the characteristic peak of the fundamental frequency $f_0$ of the reference pattern;
- band-pass filtering using a Gaussian band-pass filter, or other such filter, of this fundamental frequency $f_0$. The effect of this filtering is to remove the continuous background of the image of the reference pattern and the harmonics of the signal of the reference pattern;
- shifting of the $f_0$ filtered spectrum so as to bring the characteristic peak of the image reference pattern to the frequency 0. This shift causes the grid lines of the reference pattern to disappear, leaving only the distortions of the reference pattern;
- calculation of the inverse Fourier transform of the image, pixel column by pixel column. The image obtained reveals only the distortions. This image is a complex image comprising a real part R and an imaginary part I;
- calculation of the local phase at a pixel, modulo $2\pi$, of the image. This phase is obtained by calculating, pixel by pixel, the value of arctan (I/R).

Moreover, the Applicant has demonstrated the advantageous use of another method of calculating the local phases, namely a "wavelet transform" method of calculation. This type of calculation used in a known manner for signal processing in other applications proves to be particularly advantageous in the application of the invention. This is because, unlike the Fourier transform method, which is not a method for local analysis of the frequencies contained in the image of the reference pattern, the wavelet transform method makes it possible for the position and the frequency of the signals to be analysed simultaneously. This results in fewer perturbations at the edges of the images (at the edges of the substrate) and in better detection of small defects that are often "squashed" during the filtering phase carried out using the Fourier transform method.

The wavelet transform technique consists of several steps:
- acquisition of an image of the reference pattern distorted by the substrate;
- calculation of the wavelet coefficients W(a,b) from the image and for various values of the scale parameter a and of the translation parameter b, pixel column by pixel column (one-dimensional transform). These values are judiciously chosen according to the pitch of the reference pattern and the desired resolution. What is obtained is a wavelet scalogram;
- for each b value, search for the scale $a_0$ that maximizes the modulus $|W(a, b)|$;
- calculation of the argument of $W(a_{0,b})$ that gives at a pixel the desired local phase modulo $2\pi$;
- integration or unfolding of the phase map modulo $2\pi$ in order to obtain the absolute phase map.

Once the step of calculating the phase modulo $2\pi$ of the image has been carried out for each pixel by one or the other method, the map of the phase derivatives, also called a gradient map, is easily deduced therefrom. This calculation of the phase gradient of the image is obtained by simple difference of the phase pixel to pixel, the $2\pi$ phase jumps being easily eliminated.

After the phase map of the complete reconstructed image has been deduced from the series of images captured by the camera, it is then possible to link the derivative of the phase at each point of the image to the optical power Pi of the defects of the glazing panel causing these local phase variations by precalibrating the system using standard cylindrical lenses (in transmission) or standard cylindrical mirrors (in reflection) or else using an optical calculation model that enables the optical power Pi to be calculated from the derivative of this phase. By determining the optical power and comparing it with a threshold value, it is possible to quantify the defect.

As a variant, the phase derivative will rather be able to be compared with a local calibration width that will provide a distortion width which is also representative of the magnitude of the defect.

By quantifying the defect, it is thus possible to establish the optical quality of a glazing panel under actual conditions of use directly on the manufacturing line.

Consequently, the method according to the invention for analysing the substrate consists:
- in capturing, using a matrix camera, a series of images in transmission or in reflection of a narrow double-pattern reference pattern on said substrate without the need, as in the prior art, for studied coupling of the reference pattern relative to the camera or for use of a projector and a large screen;

in extracting from this matrix image a few columns of pixels (for example one for the horizontal reference pattern and five for the vertical reference pattern) that are associated with the double-pattern reference pattern;

in stacking, in two separate memories (one dedicated to the horizontal reference pattern and the other to the vertical reference pattern) of a processing unit for processing these columns of pixels so as to reconstruct, after the glazing panel has moved completely in front of the reference pattern (or vice versa), a complete image of each of the reference patterns seen through the glazing panel;

in extracting the local phases by digital processing, in calculating the derivative of these phases and in deducing, by mathematical calculation, the presence of a defect (preferably using an optical power calculation and its comparison with a threshold value).

Finally, the proposed measurement device permits exhaustive inspection of glazing panels present on an industrial line, without sampling them, without either stopping or slowing down the glazing panels, without modifying their position on the conveying system and without using a system for projecting two reference patterns. The device uses a small area compared with the dimensions of the reference pattern, which are much smaller than the existing ones; typically, the support panel for the reference pattern of the invention is 1.8 metres in height by 15 cm in width. Furthermore, the invention makes it possible to limit the number of acquisitions for a bidirectional analysis of the defects.

The invention claimed is:

1. A device for analysing a transparent or specular surface of a substrate comprising:
    a reference pattern facing the surface of the substrate to be measured and placed on a support with an oblong shape of shorter and longer extents, the reference pattern being bidirectional and including a first pattern that lies along a first direction and along the shorter extent of the support, the first pattern being periodic transverse to the shorter extent, and including a second pattern that lies along a second direction, perpendicular to the first pattern and along the longer extent of the support;
    a camera for capturing a plurality of images of the reference pattern distorted by the measured substrate;
    a reference pattern illumination system; and
    an image processing and digital analysis device which is connected to the camera and which constructs a single image from the plurality of images of the reference pattern distorted by the measured substrate captured by the camera so that the single image represents a whole of the substrate to identify a position of distortions on the substrate and determine the magnitude of distortions using a phase map of the reference pattern,
    wherein the camera is a matrix camera and the illumination system includes plural light-emitting diodes.

2. A device according to claim 1, wherein the first pattern and the second pattern are distinct, in an immediate vicinity of and not intersecting each other.

3. A device according to claim 1, wherein the second pattern is formed from a succession of light and dark oblong lines, a longer dimension of which lies along the longer extent of the support.

4. A device according to claim 1, wherein the second pattern is formed from a single oblong line, a longer dimension of which lies along the longer extent of the support, the line having a contrasted color relative to a background of the reference pattern.

5. A device according to claim 1, wherein the first pattern and/or the second pattern comprise/comprises at least one line which has, along its shorter extent, a width of order of 1 mm to 1 cm.

6. A device according to claim 1, wherein the first pattern includes an alternating succession of light and dark lines.

7. A device according to claim 1, wherein the support for the reference pattern includes a panel back-lit by the illumination system.

8. A device according to claim 7, wherein the support is, on its face turned towards the substrate to be measured, translucent and diffusing, or is a white plastic sheet.

9. A device according to claim 1, wherein the substrate is positioned between the reference pattern and the camera for a measurement in transmission, whereas the substrate is placed facing the reference pattern and the camera for a measurement in reflection, the camera being in a same plane as the reference pattern.

10. A device according to claim 1, wherein the reference pattern or the substrate is configured to be moved during measurement.

11. A method of analysing a transparent or specular surface of a substrate using a device according to claim 1 and such that the substrate or the reference pattern moves one relative to the other along a single displacement direction, the method comprising:
    capturing, using the matrix camera, plural images of the illuminated reference pattern in transmission or in reflection;
    spatially extracting in a periodic manner, by the camera, a column of pixels associated with the periodic first pattern and plural columns of pixels associated with the second pattern;
    stacking, in a memory, the columns of pixels for each of the patterns so as to reconstruct a single image from the plural images so that the single image represents a whole of the substrate to identify a position of distortions on the substrate; and
    analyzing the reconstructed image by digital processing so as to deduce therefrom a position of defects and to quantify the defects.

* * * * *